United States Patent
Faustman et al.

(10) Patent No.: US 9,410,144 B2
(45) Date of Patent: *Aug. 9, 2016

(54) BLOOD CELL SORTING METHODS AND SYSTEMS

(71) Applicant: The General Hospital Corporation, Boston, MA (US)

(72) Inventors: Denise L. Faustman, Boston, MA (US); Douglas E. Burger, Stoughton, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/806,112

(22) Filed: Jul. 22, 2015

(65) Prior Publication Data

US 2015/0322424 A1 Nov. 12, 2015

Related U.S. Application Data

(63) Continuation of application No. 14/291,313, filed on May 30, 2014, now abandoned, which is a continuation of application No. 13/481,237, filed on May 25, 2012, now Pat. No. 8,753,888, which is a (Continued)

(51) Int. Cl.
*C12N 13/00* (2006.01)
*G01N 1/18* (2006.01)
(Continued)

(52) U.S. Cl.
CPC .............. *C12N 13/00* (2013.01); *C12N 5/0087* (2013.01); *C12N 5/0634* (2013.01);
(Continued)

(58) Field of Classification Search
CPC .... C12N 5/0081; C12N 5/0087; C12N 13/00; Y10T 436/10; Y10T 436/101666; Y10T 436/108331; Y10T 436/25; Y10T 436/25125; Y10T 436/25375; Y10T 436/255; G01N 33/48; G01N 33/483; G01N 33/487; G01N 33/49; G01N 33/491; G01N 33/56972; G01N 33/80; G01N 1/18

USPC .......... 436/8, 10, 18, 63, 149, 150, 174, 175, 436/177, 178; 435/2, 173.9, 325; 252/408.1; 422/73, 527; 210/695
See application file for complete search history.

(56) References Cited

U.S. PATENT DOCUMENTS 3,700,555 A 10/1972 Widmark et al.
3,709,791 A 1/1973 Lichtenstein
(Continued)

FOREIGN PATENT DOCUMENTS

WO    WO 87/01607    3/1987
WO    WO 99/19730    4/1999
(Continued)

OTHER PUBLICATIONS

Brinchmann et al, "Direct immunomagnetic quantification of lymphocyte subsets in blood," Clin. Exp. Immunol., 71:182-186 (1988).
Bruno et al, "Development of an immunomagnetic assay system for rapid detection of bacteria and leukocytes in body fluids," J. Mol. Recog., 9:474-479 (1996).
Coder, "Assessment of Cell Viability," in Current Protocols in Cytometry, John Wiley & Sons Inc, pp. 9.2.1-9.2.14 (1997).
(Continued)

*Primary Examiner* — Maureen Wallenhorst
(74) *Attorney, Agent, or Firm* — Fish & Richardson P.C.

(57) ABSTRACT

The invention relates to methods of isolating white blood cells (WBCs) from a sample, e.g., whole blood, using magnetic particles that specifically bind to WBCs and a series of specific steps and conditions. The methods can include one or more of decreasing the viscosity of the sample prior to WBC isolation, agitating the sample at specified frequencies, and/or using a sample container arranged such that all of the sample is placed in close proximity (e.g., within 5, 2, 1, or 0.5 mm) to the source of the magnetic field. The new methods provide for isolation of WBC preparations with high yield, purity, and viability. The methods are designed for compatibility with automation protocols for rapid processing of multiple samples.

20 Claims, 4 Drawing Sheets

Related U.S. Application Data continuation of application No. 12/987,575, filed on Jan. 10, 2011, now Pat. No. 8,187,886, which is a continuation of application No. 11/646,985, filed on Dec. 28, 2006, now Pat. No. 7,867,765.

(60) Provisional application No. 60/754,426, filed on Dec. 28, 2005.

(51) Int. Cl.
  *G01N 33/48* (2006.01)
  *C12N 5/078* (2010.01)
  *C12N 5/00* (2006.01)
  *G01N 33/49* (2006.01)

(52) U.S. Cl.
  CPC ............ *G01N 33/491* (2013.01); *Y10T 436/10* (2015.01); *Y10T 436/101666* (2015.01); *Y10T 436/108331* (2015.01); *Y10T 436/25* (2015.01); *Y10T 436/255* (2015.01); *Y10T 436/25125* (2015.01); *Y10T 436/25375* (2015.01)

(56) References Cited

U.S. PATENT DOCUMENTS

| | | | |
|---|---|---|---|
| 4,664,796 | A | 5/1987 | Graham et al. |
| 4,910,148 | A | 3/1990 | Sorensen et al. |
| 5,155,044 | A | 10/1992 | Ledis et al. |
| 5,260,192 | A | 11/1993 | Russell et al. |
| 5,411,863 | A | 5/1995 | Miltenyi |
| 5,705,064 | A | 1/1998 | Leupold |
| 6,036,857 | A | 3/2000 | Chen et al. |
| 6,074,884 | A | 6/2000 | Siiman et al. |
| 6,194,204 | B1 | 2/2001 | Crawford et al. |
| 6,291,249 | B1 | 9/2001 | Mahant et al. |
| 6,361,749 | B1 | 3/2002 | Terstappen et al. |
| 6,417,011 | B1 | 7/2002 | Miltenyi |
| 6,451,207 | B1 | 9/2002 | Sterman et al. |
| 6,576,428 | B1 | 6/2003 | Assenmacher et al. |
| 6,586,259 | B1 | 7/2003 | Mahan et al. |
| 7,326,350 | B2 | 2/2008 | Mueller et al. |
| 7,867,765 | B2 | 1/2011 | Faustman et al. |
| 8,187,886 | B2 | 5/2012 | Faustman et al. |
| 8,753,888 | B2 | 6/2014 | Faustman et al. |
| 2004/0265903 | A1 | 12/2004 | Mueller et al. |
| 2007/0163963 | A1 | 7/2007 | Faustman et al. |

FOREIGN PATENT DOCUMENTS

| | | |
|---|---|---|
| WO | WO 2004/013155 | 2/2004 |
| WO | WO 2007/079149 | 7/2007 |

OTHER PUBLICATIONS

Cox et al., "Automating Procedures for Processing, Cryopreservation, Storage, and Manipulation of Human Peripheral Blood Mononuclear Cells," JALA, 9:16-23 (2004).

Decision to grant a European Patent issued in 06848249.6 on Oct. 31, 2013 (1 page).

Dynal Biotech, "CD8 Positive Isolation Kit," Jul. 2, 2003.

European Communication issued in 06848249.6 on Dec. 6, 2010 (3 pages).

European Communication Under Rule 71(3) EPC issued in 06848249.6 on Jul. 10, 2013 (50 pages).

European Search Report issued in 06848249.6 on Jul. 16, 2009 (8 pages).

Final Office Action issued in U.S. Appl. No. 11/646,985 on Mar. 23, 2010, Examiner Maureen Wallenhorst (10 pages).

Final Office Action issued in U.S. Appl. No. 12/987,575 on Oct. 20, 2011, Examiner Maureen Wallenhorst (8 pages).

Final Office Action issued in U.S. Appl. No. 13/481,237 on Apr. 4, 2013, Examiner Maureen Wallenhorst (8 pages).

International Search Report and Written Opinion issued in PCT/US2006/049437, dated Jul. 18, 2007; 8 pages.

Miltenyi Biotec, "Whole Blood CD8 MicroBeads," 140-000-684.03 (2005).

Non-Final Office Action issued in U.S. Appl. No. 11/646,985 on Jun. 9, 2009, Examiner Maureen Wallenhorst (15 pages).

Non-Final Office Action issued in U.S. Appl. No. 12/987,575 on May 2, 2011, Examiner Maureen Wallenhorst (17 pages).

Non-Final Office Action issued in U.S. Appl. No. 13/481,237 on Sep. 10, 2012, Examiner Maureen Wallenhorst (17 pages).

Notice of Allowance and Interview Summary issued in U.S. Appl. No. 11/646,985 on Sep. 8, 2010 (9 pages).

Notice of Allowance issued in U.S. Appl. No. 12/987,575 issued on Jan. 30, 2012 (7 pages).

Notice of Allowance issued in U.S. Appl. No. 13/481,237 on Feb. 11, 2014 (5 pages).

Rasmussen et al, "A new method for detachment of Dynabeads from positively selected B lymphocytes," J. Immunol Meth., 146:195-202 (1992).

Rosenson et al., "Distribution of blood viscosity values and biochemical correlates in healthy adults," Clin. Chem., 42:1189-95 (1996).

Safarik et al, "Use of magnetic techniques for the isolation of cells," J. Chromatogr. B Biomed. Sci. Appl., 722:33-53 (1999).

Sorenson et al., "Distribution of blood viscosity values and biochemical correlates in healthy adults," Clin. Chem. 42:1189-95 (1996).

Supplemental Search Report issued in EP 06 84 8249, PCT/US2006/049437, dated Jul. 16, 2009; 8 pages.

BLOOD CELL SORTING METHODS AND SYSTEMS

CROSS-REFERENCE TO RELATED APPLICATIONS

This application is a continuation of U.S. application Ser. No. 14/291,313, filed on May 30, 2014, now abandoned, which is a continuation of U.S. application Ser. No. 13/481,237, filed on May 25, 2012, and issued as U.S. Pat. No. 8,753,888, which is a continuation of U.S. application Ser. No. 12/987,575, filed on Jan. 10, 2011, and issued as U.S. Pat. No. 8,187,886, which is a continuation of U.S. application Ser. No. 11/646,985, filed on Dec. 28, 2006, and issued as U.S. Pat. No. 7,867,765, which claims the benefit of U.S. Provisional Application No. 60/754,426, filed on Dec. 28, 2005. The contents of the foregoing applications are incorporated herein by reference in their entireties.

BACKGROUND

There are many clinical settings where tests on the viable white blood cells or subpopulations of blood cells are desired. For instance, in the HIV/AIDS field it would be of benefit to know if specific T cell subpopulations are present in the blood and are capable of eliciting an immune response to the virus. In the vaccination clinical trial arena, it is desirable to know if an immunization induces the formation of disease fighting cells. In the field of autoimmunity it is important to both isolate pathogenic T cells and perform functional studies on these cells.

High throughput screening of white blood cells (WBCs) is desirable, particularly for investigations in personalized medicine and a patient's response to drugs. This is difficult if the starting method is gradient separation of whole blood, because this method is not easily automated. Furthermore it is desirable clinically to separate blood in a fashion that yields different populations of blood cells each time with different starting viabilities. There is an unmet need for automation of whole blood separation of WBCs with reproducibly high viability, yield, and purity.

The functional and cell surface traits of white blood cells cannot be easily examined without these cells being physically separated from the red blood cells (RBCs). However, functional and quantitative examination of WBCs, or subpopulations of WBCs in blood samples has been hampered by the fact that blood is composed RBCs, which exceed the number of WBCs by a ratio of greater than 10,000:1. Separations are further hampered by the viscosity of whole blood, due to the serum and the density of cells per cubic centimeter.

A number of principles have been applied to separate RBCs from various populations of WBCs. Traditionally, gradient separations have been used. Gradient separations work on the principle that RBCs are small and dense, and can form a pellet when centrifuged, usually below a "cushion" of a substance such as Ficoll. Although effective, the gradient methods are typically slow, difficult to automate, not reproducible, give poor yields, and produce cells with poor viability. Also, the final product often contains remaining RBC contamination that requires additional processing steps (e.g., RBC lysis) to remove the inadequately separated cells.

Another commonly used method to separate blood for functional assays and clinical diagnostics is direct RBC lysis. The principle of this method is that the RBCs are more sensitive to changes in the osmolarity of the media than WBCs, such that a brief and fast change in the osmolarity of the medium or buffer will lyse more RBCs than WBCs. Indeed, lysis methods work, but as with gradient methods, the reproducibility of the separation and the viability and numbers of the remaining WBCs cells are typically poor and not representative of the whole population. Damage to WBCs can also occur with these lysis methods.

A more recently developed technology to separate subpopulations of blood cells has utilized magnetic particles to separate blood cells. This typically works by one of two principles. The first method involves positive selection by the use of magnetically labeled antibodies that bind to cell surface markers of the desired WBCs (or a cellular subpopulation of WBCs, e.g., T cells, B cells, NK cells, monocytes, dendritic cells, granulocytes, or leukocytes). The second method involves negative selection by the use of magnetically labeled antibodies to cell surface markers of RBCs or other populations to be removed. Although these methods often produce higher quality WBC preparations than gradient separations or lysis methods, it is still difficult to reproducibly obtain a WBC preparation from whole blood with high viability, yield, and purity. Specific methods for magnetic separation of WBCs are described, for example, in U.S. Pat. Nos. 4,910,148; 5,411,863; 6,417,011; and 6,576,428. Kits for performing magnetic separations are commercially available, e.g., from Dynal Biotech (Oslo, Norway) and Miltenyi Biotech (Bergisch Gladbach, Germany).

Most blood protocols utilize enrichment of WBC preparations prior to the application of magnetic particles. Such enrichment procedures can involve gradient separations, RBC lysis, or retrieval of a minor portion of the total WBC populations by buffy coat harvests from drawn blood. These partially enriched preparations of cells are then subsequently used with the magnetic particles for positive or negative selections.

Harvesting white blood cells or white blood cell subpopulations from whole blood can be challenging due to the higher abundance of red blood cells compared to that observed in bone marrow, lymph node or splenic preparations.

SUMMARY

The invention is based, in part, on the discovery that by following a specific series of method steps, e.g., in certain orders and using certain conditions, one can reproducibly obtain white blood cell (WBC) preparations from blood samples, e.g., whole blood, with high viability, yield, and purity, e.g., each over 80% or 90%. The methods can include one or more of decreasing the viscosity of the sample prior to WBC isolation, agitating the sample, and using a sample container arranged such that the entire sample is placed in close proximity (e.g., within 5, 4, 3, 2, 1, or 0.5 mm) to the source of the magnetic field. The methods described herein can provide improved purity, viability, and yield compared to conventional isolation methods.

The invention features methods of isolating white blood cells or a subset or fraction of white blood cells from a sample by (a) obtaining a sample including whole blood or a blood fraction that includes white blood cells; (b) decreasing viscosity of the sample; (c) contacting the sample with a magnetic particle that binds specifically to white blood cells or a subset of white blood cells to provide a white blood cell/magnetic particle complex; (d) isolating the white blood cell/magnetic particle complex by subjecting the white blood cell/magnetic particle complex to a magnetic field at a strength and for a time sufficient to achieve a final cell yield of greater than 75% (e.g., greater than 80%, 85%, 90%, 95%, or 98%); and optionally (e) removing the magnetic particles from the cells in the complexes, thus isolating white blood cells with a cell yield of greater than 75% (e.g., greater than 80%, 85%, 90%, 95%, or 98%).

In some embodiments, the methods further include agitating the sample in step (c) at a frequency sufficient to improve efficiency of binding of the magnetic particles to the cells and/or agitating the white blood cell/magnetic particle complex in step (e) at a frequency sufficient to improve efficiency of removal of the magnetic particle.

In various embodiments, decreasing viscosity involves replacing a liquid component of the sample, e.g., blood or blood fraction, or washing the cells in the sample, or diluting the sample, with a solution, e.g., an isotonic solution (e.g., a salt solution, such as phosphate buffered saline or Hank's balanced salts solution, or a cell medium) that includes a proteinaceous additive (e.g., serum or serum albumin at 0.1 to 10%, e.g., serum at 2 to 5%). In certain embodiments, decreasing viscosity involves reducing the pH of the blood or blood fraction.

In some embodiments, the time sufficient to achieve a final cell yield of greater than 75% (e.g., greater than 80%, 85%, 90%, 95%, or 98%) is greater than 10 minutes (e.g., greater than 20, 30, 60, 90, or 120 minutes). In some embodiments, the time sufficient to achieve a final cell yield greater than 75% (e.g., greater than 80%, 85%, 90%, 95%, or 98%) is less than 120 minutes (e.g., less than 90, 60, 30, 20, or 15 minutes).

In some embodiments, the white blood cell/magnetic particle complex is subjected to a magnetic field in a vessel with walls less than about less than 0.8 mm (e.g., less than 0.7, 0.65, 0.6, 0.5, 0.2, or 0.1 mm) thick. In some embodiments, the white blood cell/magnetic particle complex is subjected to a magnetic field in a vessel such that the white blood cell/magnetic particle complex is within 5 mm (e.g., within 4, 3, 2, 1, or 0.5 mm) of a source of the magnetic field, e.g., a magnet.

In some embodiments, the agitating includes agitating, shaking, or vibrating (e.g., in an orbital or linear motion) the sample at a frequency and with an amplitude such that the magnetic particles are maintained substantially in suspension. For example, the sample can be agitated, shaken, or vibrated such that, at steady state, a test sample removed from near the top of the liquid column in the vessel has about the same number (e.g., about 80%, 85%, 90%, or 95% of the number) of magnetic particles per unit volume as a test sample removed from near the bottom of the liquid column. In some embodiments, the step of agitating includes agitating, shaking, or vibrating (e.g., in an orbital or linear motion) the sample in a vessel at a frequency of about 400, 500, 600, 700, 800, 900, or 1000 rpm and with an amplitude of about 2%, 3%, 4%, 5%, 6%, 7%, or 8% of the height of the liquid column in the vessel or about 10%, 15%, 20%, 30%, 35%, or 40% of a dimension of the width of the liquid column in the vessel (e.g., a maximum diameter of the liquid column). In some embodiments, the step of agitating includes agitating, shaking, or vibrating (e.g., in a circular or linear motion) at a frequency of about 400, 500, 600, 700, 800, 900, or 1000 rpm and with an amplitude of about 1, 1.5, 2, 2.5, 3, 4, 5, 10, or 20 mm.

However, in some other embodiments, the methods do not include any significant mixing (e.g., tilting, rocking, rotating, or oscillating).

In certain embodiments, following the isolating step and prior to the removing step, the methods further include washing the white blood cell/magnetic particle complex, e.g., with a solution, e.g., an isotonic solution (e.g., a salt solution, such as phosphate buffered saline or Hank's balanced salts solution, or a cell medium) that includes a proteinaceous additive (e.g., serum or serum albumin at 0.1 to 10%, e.g., serum at 2 to 5%), and subjecting the washed white blood cell/magnetic particle complex to the magnetic field. In some embodiments, the time between washing the white blood cell/magnetic particle complex and subjecting the washed white blood cell/magnetic particle complex to the magnetic field is at least 5 minutes (e.g., at least 10, 15, 20, or 30 minutes).

In some embodiments, the methods include adding an anticoagulant to the sample or white blood cell/magnetic particle complex before, during, or after any of the method steps.

The invention also features methods of isolating a sample, e.g., containing white blood cells or a subset or fraction of white blood cells, by (a) obtaining a sample that includes whole blood or a blood fraction that includes white blood cells; (b) contacting the sample with a magnetic particle that binds specifically to white blood cells or a subset of white blood cells to provide a white blood cell/magnetic particle complex; (c) during step (b), agitating the magnetic particle and blood or blood fraction at a frequency sufficient to improve efficiency of binding of the magnetic particles to the white blood cells or subset of white blood cells; (d) isolating the white blood cell/magnetic particle complex by subjecting the white blood cell/magnetic particle complex to a magnetic field at a strength and for a time sufficient to achieve a final cell yield of greater than 75% (e.g., greater than 80%, 85%, 90%, 95%, or 98%); and optionally (e) removing the magnetic particles from the cells in the complexes, thus isolating white blood cells with a cell yield of greater than 75% (e.g., greater than 80%, 85%, 90%, 95%, or 98%). In some embodiments, the methods further include agitating the white blood cell/magnetic particle complex at a frequency sufficient to improve efficiency of removal of the magnetic particle. In some embodiments, the methods further include decreasing viscosity of the blood or blood fraction prior to step (b).

The invention further includes compositions of white blood cells with a white blood cell yield of greater than 75% (e.g., greater than 80%, 85%, 90%, 95%, or 98%), prepared by the new methods. In some embodiments, the white blood cell purity of the composition is greater than 80% (e.g., greater than 85%, 90%, 95%, 98%, or 99%).

The invention also includes methods of removing white blood cells or a subset or fraction of white blood cells from a blood sample by (a) obtaining a sample including whole blood or a blood fraction that includes white blood cells; (b) decreasing viscosity of the sample; (c) contacting the sample with a magnetic particle that binds specifically to white blood cells or a subset of white blood cells to provide a white blood cell/magnetic particle complex; (d) removing the white blood cell/magnetic particle complex by subjecting the white blood cell/magnetic particle complex to a magnetic field at a strength and for a time sufficient to achieve a final cell removal of greater than 75% (e.g., greater than 80%, 85%, 90%, 95%, or 98%); and optionally (e) isolating the uncomplexed cells, thus isolating a blood sample lacking greater than 75% (e.g., greater than 80%, 85%, 90%, 95%, or 98%) of the original white blood cells or the original subset of white blood cells. In some embodiments, the methods further include agitating the white blood cells and magnetic particles at a frequency sufficient to improve the efficiency of binding of the white blood cells to the magnetic particles.

In various embodiments, decreasing viscosity involves replacing a liquid component of the sample, e.g., blood or blood fraction, washing the cells of the sample, or diluting the sample, with a solution, e.g., an isotonic solution (e.g., a salt solution, such as phosphate buffered saline or Hank's balanced salts solution, or a cell medium) that includes a proteinaceous additive (e.g., serum or serum albumin at 0.1 to 10%, e.g., serum at 2 to 5%). In some embodiments, decreasing viscosity involves reducing the pH of the blood or blood fraction.

In some embodiments, the time sufficient to achieve a final cell yield of greater than 75% (e.g., greater than 80%, 85%, 90%, 95%, or 98%) is greater than 10 minutes (e.g., greater than 20, 30, 60, 90, or 120 minutes). In some embodiments, the time sufficient to achieve a final cell yield greater than 75% (e.g., greater than 80%, 85%, 90%, 95%, or 98%) is less than 120 minutes (e.g., less than 90, 60, 30, 20, or 15 minutes).

In some embodiments, the white blood cell/magnetic particle complex is subjected to a magnetic field in a vessel with walls less than about less than 0.8 mm (e.g., less than 0.7, 0.65, 0.6, 0.5, 0.2, or 0.1 mm) thick. In some embodiments, the white blood cell/magnetic particle complex is subjected to a magnetic field in a vessel such that the white blood cell/magnetic particle complex is within 5 mm (e.g., within 4, 3, 2, 1, or 0.5 mm) of a source of the magnetic field.

In some embodiments, the step of agitating includes agitating, shaking, or vibrating (e.g., in an orbital or linear motion) the sample at a frequency and with an amplitude such that the magnetic particles are maintained substantially in suspension. For example, the sample can be agitated, shaken, or vibrated such that, at steady state, a test sample removed from near the top of the liquid column in the vessel has about the same number (e.g., about 80%, 85%, 90%, or 95% of the number) of magnetic particles per unit volume as a test sample removed from near the bottom of the liquid column. In some embodiments, the step of agitating includes agitating, shaking, or vibrating (e.g., in a orbital or linear motion) the sample in a vessel at a frequency of about 400, 500, 600, 700, 800, 900, or 1000 rpm and with an amplitude of about 2%, 3%, 4%, 5%, 6%, 7%, or 8% of the height of the liquid column in the vessel or about 10%, 15%, 20%, 30%, 35%, or 40% of a dimension of the width of the liquid column in the vessel (e.g., a maximum diameter of the liquid column).

In some embodiments, the step of agitating includes agitating, shaking, or vibrating (e.g., in an orbital or linear motion) at a frequency of about 400, 500, 600, 700, 800, 900, or 1000 rpm and with an amplitude of about 1, 1.5, 2, 2.5, 3, 4, 5, 10, or 20 mm. In some embodiments, the methods do not include mixing (e.g., tilting, rocking, rotating, or oscillating) the sample at an amplitude greater than about 3, 4, 5, 10, 20, 30, or 40 mm.

As used herein, amplitude is a measure of the distance the vessel or container is moved, e.g., from side to side, when agitated.

In some embodiments, the methods include adding an anticoagulant to the sample, e.g., whole blood or blood fraction, or white blood cell/magnetic particle complex before, during, or after any of the method steps.

The invention further includes compositions of blood cells lacking greater than 75% (e.g., greater than 80%, 85%, 90%, 95%, or 98%) of the original white blood cells or the original subset of white blood cells, prepared by the new methods.

The invention also includes methods of removing white blood cells or a subset or fraction of white blood cells from a blood sample by (a) obtaining a sample including whole blood or a blood fraction that includes white blood cells; (b) contacting the sample with a magnetic particle that binds specifically to white blood cells or a subset of white blood cells to provide a white blood cell/magnetic particle complex; (c) during step (b), agitating the magnetic particle and sample at a frequency sufficient to improve efficiency of binding of the magnetic particles to the white blood cells or subset of white blood cells; (d) removing the white blood cell/magnetic particle complex by subjecting the white blood cell/magnetic particle complex to a magnetic field at a strength and for a time sufficient to achieve a final cell removal of greater than 75% (e.g., greater than 80%, 85%, 90%, 95%, or 98%); and optionally (e) isolating the uncomplexed cells, thus isolating a blood sample lacking greater than 75% (e.g., greater than 80%, 85%, 90%, 95%, or 98%) of the original white blood cells or the original subset of white blood cells. In some embodiments, the methods further include agitating the white blood cells and magnetic particles at a frequency sufficient to improve the efficiency of binding of the white blood cells to the magnetic particles.

The invention also includes methods of isolating white blood cells or a subset of white blood cells from a sample by (a) obtaining a sample including whole blood or a blood fraction that includes white blood cells; (b) decreasing viscosity of the sample; (c) contacting the sample with a magnetic particle that binds specifically to white blood cells or a subset of white blood cells to provide a white blood cell/magnetic particle complex; (d) isolating the white blood cell/magnetic particle complex by subjecting the white blood cell/magnetic particle complex to a magnetic field; and optionally (e) removing the magnetic particles from the cells in the complexes, thus isolating white blood cells.

The invention also includes kits that include one or more magnetic particles that bind specifically to white blood cells or to a subset of white blood cells and instructions to perform the new methods. The kits can also include a magnetic field source or a vessel with walls less than about less than 0.8 mm (e.g., less than 0.7, 0.65, 0.6, 0.5, 0.2, or 0.1 mm) thick.

The invention also features systems and computer or machine-implemented programs for carrying out the methods described herein. The programs include a plurality of program instructions stored on an electronic apparatus-readable medium for implementing the steps of the methods described herein.

The new methods described in this application eliminate gradient separations, a process difficult to automate and difficult to perform reproducibly. The methods also eliminate toxic treatment of cells with lysis buffers, a process that yields purity, but at the expense of viability and full yield of the cells. The methods proposed allow whole blood separations of white bloods, either with positive or negative selection, and these methods are fully capable of being automated, since the steps involved utilize liquid handling and pipetting. These methods are also valuable with manual or automated performance of these procedures for white blood cell compositions of high purity, high viability, and high yield. In addition, the new methods provide high-quality cells useful in functional assays to detect defects in blood with small sample sizes. The use of these high quality cell compositions provides greater reproducibility of data compared to the use of cell compositions obtained by prior methods.

The new methods provide for isolation of WBC preparations with high yield, purity, and viability. Furthermore, the steps of the new methods can be easily automated for rapid processing of multiple samples.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

In addition, the materials, methods, and examples are illustrative only and not intended to be limiting.

Other features and advantages of the invention will be apparent from the following detailed description, and from the claims.

DETAILED DESCRIPTION

Figure 1:
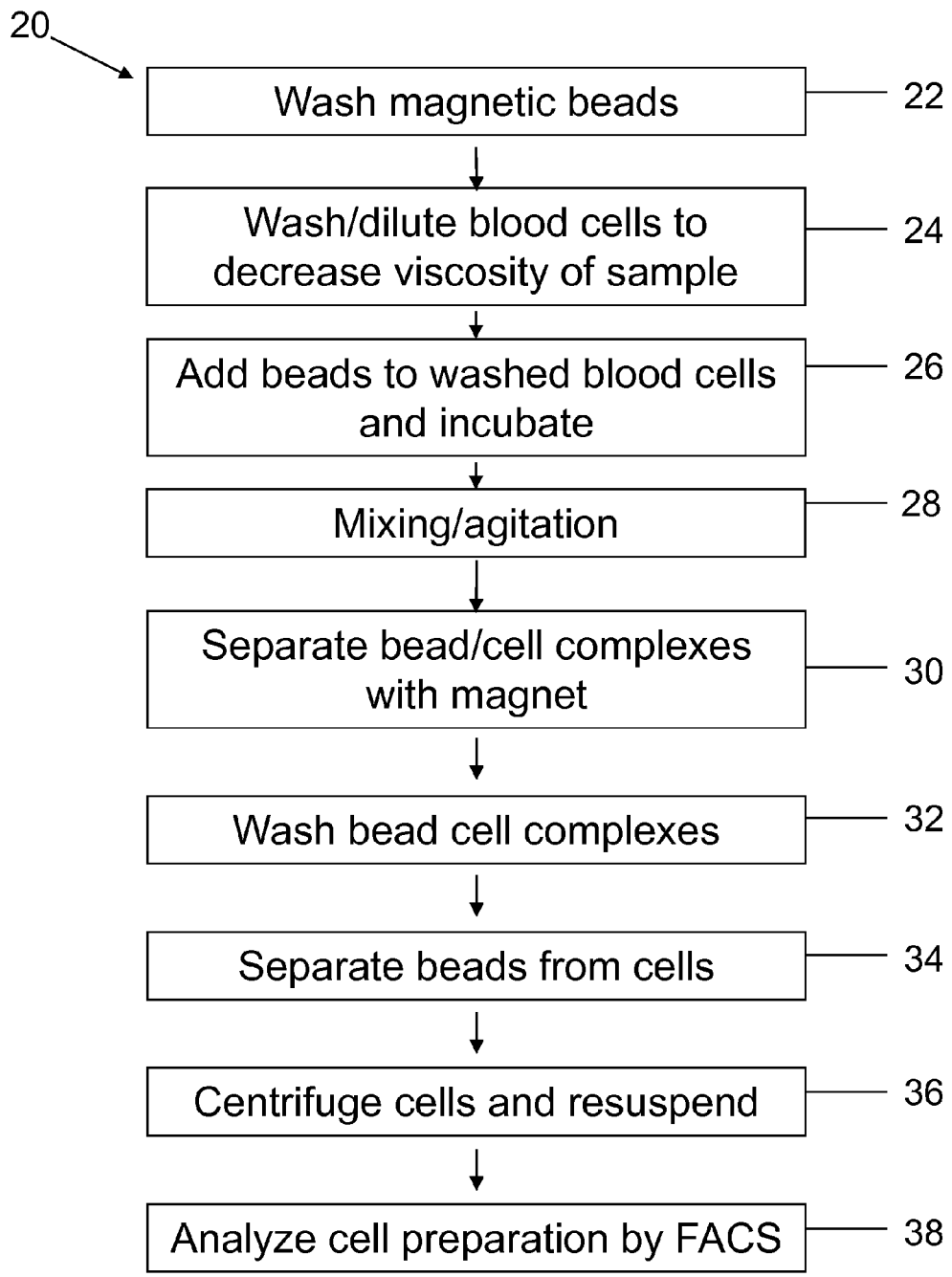
FIG. 1 is a flowchart showing an exemplary set of steps for a cell preparation using the new methods. These steps can be performed by an automated laboratory system.

The invention relates to methods of isolating white blood cells (WBCs) from a sample, e.g., whole blood, using magnetic particles that bind to WBCs and a series of specific steps and conditions. The methods include decreasing the viscosity of the sample prior to WBC isolation, agitating the sample to improve the efficiency of binding of the magnetic particles to the white blood cells, and/or using a sample container arranged such that all of the sample is placed in close proximity (e.g., within 5, 4, 3, 2, 1, or 0.5 mm) to the source of the magnetic field. The new methods provide for isolation of WBC preparations with high yield, purity, and viability. Furthermore, the steps of the new methods can be easily automated for rapid processing of multiple samples.

Magnetic methods of separating WBCs from blood samples are known and typically include mixing a sample containing blood cells (e.g., whole blood or a blood fraction) with magnetic particles conjugated to a binding member, e.g., an antibody, that specifically binds to WBCs or a subpopulation of WBCs (e.g., T cells, B cells, NK cells, monocytes, dendritic cells, granulocytes, or leukocytes), and separating the magnetic particle-bound cells from the sample using a magnetic field. Kits for performing magnetic separations are commercially available, e.g., from Dynal Biotech (Oslo, Norway) and Miltenyi Biotech (Bergisch Gladbach, Germany).

Subpopulations or subsets of WBCs expressing specific cell surface proteins can be separated by utilization of magnetic particles conjugated to binding members specific for those proteins. Exemplary cell surface proteins include CD2, CD3, CD4, CD8, CD14, CD15, CD16, CD19, CD25, CD28, CD34, CD45, CD56, BMLF-1, LMP2, cytomegalovirus pp65, Her-2/neu, MART-1, gp100 (209-2M), and hTERT.

The new methods are improvements of the methods using such magnetic particles and can be used to isolate WBCs from any sample, e.g., tissue or fluid sample, that contains WBCs, preferably blood, e.g., whole blood. In some embodiments, the sample is whole blood, buffy coat, or a suspension of mononuclear cells (MNC). The sample can further include an anticoagulant, such as EDTA, heparin, citrate dextrose formula-A (ACD-A) or citrate phosphate dextrose (CPD). Whole blood can be from an animal (e.g., a mouse, rat, or rabbit) or from a human. Whole blood can be stored, e.g., with refrigeration, prior to separation. In other embodiments, the whole blood is used fresh, i.e., without storing.

Any blood fraction that contains WBCs can be used in the methods described herein. Preparation of blood fractions are well known in the art. For example, a buffy coat can be prepared by centrifuging a whole blood sample at about 200 g at room temperature and removing the band or layer that contains primarily leukocytes. Typically, this procedure yields a preparation with about 30 RBCs for each WBC. The use of gradients typically excludes the possibility of using automation. The complex process of visually extracting cells from a "fuzzy" interface between the variable gradients is difficult to perform without human input.

General Methodology

FIG. 1 is a flowchart that shows an exemplary set of steps 20 for a cell preparation using the new methods. These steps can be performed by an automated laboratory system. A sample that includes WBCs, e.g., whole blood, is treated to reduce viscosity (e.g., by washing the cells one, two, three, or more times with an isotonic solution, such as Hank's Balanced Salts Solution (HBSS) with 2% to 5% serum, and also containing an anticoagulant, such as ACD)(step 24). Magnetic beads that bind to the desired WBC population, e.g., from Dynal Biotech (Oslo, Norway), are optionally washed (step 22) and added to the blood sample and the mixture is incubated for 30 minutes or more (e.g., 45 minutes, 1 hour, or more) to allow the beads to bind to the WBCs (step 26).

Optionally, the sample is agitated during bead binding to improve binding efficiency (step 28).

Following binding to the magnetic beads, the cells are separated from the sample (step 30) by subjecting the white blood cell/magnetic particle complex to a magnetic field at a strength and for a time sufficient to achieve a final cell yield of greater than 75% (e.g., 80%, 85%, 90%, 95%, 98% or greater). The unbound supernatant is removed, e.g., using a pipette or aspirator, and the magnetically attracted cells are washed up to four times with the isotonic solution (step 32). For each wash, about a sample volume of isotonic solution is added to the magnetically bound cells, and the cells are allowed a period to re-attract to the magnet.

After the first wash step, this magnet re-attraction period should be at least 10 minutes to ensure binding of cells to the beads and magnetic attraction. For high purity (e.g., about 98%), all of the supernatant is removed from the tube after each wash. For better yield with about 95% purity, it is necessary to leave a small amount (about a tenth to a fifth of a sample volume) of supernatant in the tube following each wash. Thin-walled tubes should be used in all steps involving magnetic attraction.

Following binding and washing, the cells and magnetic beads are separated (step 34), e.g., using a commercially available detachment solution (e.g., from Dynal) as described by the manufacturer. Optionally, the complexes can be agitated during detachment of the cells from the magnetic beads, and the cells can be centrifuged and resuspended (step 36). As discussed in further detail below, agitation is typically done using a vibration of at least about 200 or 400 to about 1000 rpm, e.g., at least about 700 or 800 rpm, and at an amplitude of about 1-20 mm (e.g., about 1-2, 1-5, 1-10, 2-5, 2-10, 2-20, 5-10, 1-3, 2-4, or 5-20 mm).

Optionally, cell yield is estimated by comparing the number of cells obtained, e.g., as measured by flow cytometry, to an estimate of the average number of the population of WBCs in the sample, e.g., human blood (e.g., $0.388 \times 10^6$ cells/ml for $CD8^+$ cells in human blood), or to a count of the number of the population of WBCs in the sample prior to processing (step 38).

Viability and purity of the isolated WBCs, such as $CD8^+$ cells, are measured using standard techniques, e.g., flow cytometry. For example, 50 µl of a cell preparation can be mixed with 200 µl of 5 µg/ml propidium iodide (PI) and FITC-conjugated antibody that binds specifically to the population of isolated WBCs. Dead cells can be identified by PI fluorescence. The desired WBCs will have fluorescence from FITC, whereas heterologous cells will not.

The new methods can produce preparations of WBC preparations with 75% or greater cell yield (e.g., 80%, 85%, 90%, 95%, 98%, 99% or greater), 90% or greater cell viability (e.g., 92%, 95%, 98%, 99% or greater), and 80% or greater cell purity (e.g., 85%, 90%, 95%, 98%, 99% or greater).

Following isolation of WBCs, the cells can be "rested" before any downstream analysis by allowing the cells to remain undisturbed in cell culture medium or an isotonic solution for a period of about 2 hours to about 6 days, e.g., 2, 4, 6, 12, 15, 20, or 24 hours or 2, 3, 4, 5, or 6 days. This rest period can allow the cells to recover from any effects or damage the preparation method may have caused the cells.

Alternatively, the new methods can be used for negative selection of WBCs, i.e., to remove WBCs or a population of WBCs from a sample that includes WBCs, e.g., whole blood. For negative selection of WBCs, the method is performed as above, a sample that includes WBCs, e.g., whole blood, is treated to reduce viscosity (e.g., by washing the cells one, two, three, or more times with an isotonic solution, such as Hank's Balanced Salts Solution (HBSS) with 2% to 5% serum, and also containing an anticoagulant, such as ACD). Magnetic beads that bind to the WBC population one wants to remove, e.g., from Dynal Biotech (Oslo, Norway), are added and the mixture is incubated for 30 minutes or more (e.g., 45 minutes, 1 hour, or more) to allow the beads to bind to the WBCs. Optionally, the mixture is agitated to improve efficiency of binding of the beads to the cells. Following binding to the magnetic beads, the cells are separated using a magnet device. The unbound supernatant, which is substantially free (e.g., more than 75% free (e.g., more than 80%, 85%, 90%, 95%, 98%, or 99% free) of WBCs is removed and used for downstream processes. The methods described herein can be used for positive and/or negative selection of WBCs.

Methods of Decreasing Sample Viscosity

When separating WBCs from a blood sample, it is advantageous to decrease the viscosity of the blood prior to separation methods. This step allows for increased yield or removal of WBCs in the final preparation. Typically, the viscosity of the blood sample is decreased by pre-washing of the blood cells or dilution of the blood sample.

In some embodiments, the viscosity of the blood sample can be decreased by pre-washing the blood sample to remove the viscous serum. Typically, the blood is pre-washed by removing the cells from the serum (e.g., by centrifugation or filtration), and re-suspending the cells in a fluid matrix, e.g., media or a buffer (e.g., PBS). The fluid matrix can contain one or more additives, such as a proteinaceous additive (e.g., calf serum or BSA at about 0.1 to 10%) or an anticoagulant. The step of washing can include multiple independent washes of removing the cells and re-suspending the cells in a fluid matrix. To achieve an optimal yield, care can be taken at each wash step not to lose cells of the sample, e.g., by taking care not to disturb the pellet following a centrifugation step.

In other embodiments, the viscosity of the blood sample can be decreased by dilution of the blood sample. The diluent can be an aqueous solution, e.g., an isotonic solution, such as media or a buffer (e.g., PBS). Typically, the blood sample is diluted with 2 to 50 sample volumes, e.g., 3, 4, 5, 10, 20, 30, or 40 sample volumes, of diluent. Dilution with greater than 50 sample volumes can be useful when the diluted sample size can be large. The diluent can contain one or more additives, such as a proteinaceous additive (e.g., calf serum or BSA at about 0.1 to 10%) or an anticoagulant.

The viscosity can be reduced by other means. For example, the whole blood components that are responsible for viscosity of the sample can be specifically or non-specifically removed, degraded, or cleaved. Alternately, the pH of the whole blood can be reduced, e.g., by addition of an acid to the sample. The pH of the sample can be monitored or otherwise adjusted such that the viability of the cells in the sample is maintained at a desired level.

Furthermore, anti-coagulant can be added throughout the separation process to ensure the blood remains fluid and the cells do not clump.

The viscosity of the sample can be measured by any means known in the art, e.g., using a viscometer (e.g., a capillary or cone-in-plate viscometer). The measured viscosity of the sample can be less than 3.0 mPa·s, e.g., less than 2.5, 2.0, 1.75, 1.5, 1.25, 1.0, or 0.5 mPa·s.

Magnetic Separations

To optimize the yield and other properties of a magnetic separation method, it is useful to increase the magnitude of the magnetic field (e.g., the magnetic field strength) that acts on each of the cell-bound magnetic particles. This can be accomplished by increasing the strength of the magnet, decreasing the distance between the particles and the magnetic source, or increasing the time during which the sample is exposed to the magnetic field.

Typically, relatively strong magnets are used for magnetic separations. Commercially available systems use strong rare earth magnets (e.g., neodymium-iron-boron permanent magnets). Strong electromagnets can also be suitable for performing magnetic separations. The magnet can be arranged to optimize the magnetic field strength within the magnetic particle-containing sample. The magnetic field strength of the magnet (source) should be between about 20 and 500 kA/m (e.g., about 50, 100, 150, 200, 250, 300, 350, 400, 500, 600, 750, or even 1000 kA/m). Better results are obtained using a magnetic field strength of at least about 300 kA/m.

Since the strength of the magnetic field decreases with distance from the magnetic source, it is preferable to place as much of the sample as possible within the vicinity of the magnet. To accomplish this, the magnetic particle-containing sample can be held in a thin-walled vessel, e.g., a vessel with walls less than 0.8, 0.7, 0.65, 0.6, 0.5, 0.2, or 0.1 mm. Additionally, the vessel holding the magnetic particle-containing sample can be arranged such that much or all of the sample is in close proximity to the magnet, e.g., within 5, 4, 3, 2, 1, or 0.5 mm of the magnet. For example, a vessel with at least one surface that matches the conformation of the surface of the magnet can be used, e.g., a vessel with a planar or nearly planar surface area can be arranged to interact with a planar or nearly planar magnet. In other embodiments, the vessel is designed such that the cross-section perpendicular to the magnet at the vessel/magnet interface is small relative to the magnetic field strength.

Cryogenic vials can be used in the methods described herein. These are typically sterile cylindrical vessels with thin walls (e.g., less than 0.8 mm) that can hold between 1 and 2 ml. They can be arranged with one or more magnets such that much or all of the sample is in close proximity to the magnet (e.g., within 5 mm). An exemplary system is described below, with a plate adapted to hold 24 cryogenic vials in a 6×4 configuration with 15 tall cylindrical magnets intercalated between the sample vials.

Additionally, extending the period of time during which the magnetic particle-containing sample is exposed to the magnetic field can allow more of the sample to be attracted to the magnet and retained. The time during which the sample is exposed to the magnetic field can be optimized to a desired total sample processing time. The total processing time may, in some instances, affect the viability or other properties of the final WBC product.

Agitation

Specific methods of agitation can be used to improve the yield, purity, and/or viability of the WBC preparation. Typically, known sample preparation methods utilize mechanisms that tilt, rotate, or rock the blood tube with large rotations to maintain the cells and magnetic particles in suspension to facilitate binding of the cells to the particles. In general, these devices permit the magnetic beads to be agitated at a frequency that exceeds Brownian motion. Typical devices tilt, rotate, or rock the sample at low frequencies (~0.5 Hz) with large amplitudes of oscillation (cm scale) in an attempt to mix the sample thoroughly, but gently so as not detach bead-cell complexes. Such devices include the Variomag Thermoshake™ (Inheco, Munich, Germany), Dynal® Sample Mixer (Invitrogen, Carlsbad, Calif.), and Boeker Orbitron Rotators (Feasterville, Pa.).

It has been discovered that agitation of blood cell-containing samples at higher frequencies and lower amplitudes provides advantages over known methods of rocking, rotating, and shaking Agitation methods can provide higher cell yield and are more suitable to automation than prior methods. Agitation allows for ease of automation by not requiring a procedure for capping and uncapping the sample tubes, and also by utilizing smaller amplitude oscillations (vibrations), allowing for ease of integration of the agitation mechanism with existing automation platforms.

Samples containing cells and magnetic particles are agitated (e.g., shaken or vibrated) at a frequency and with an amplitude such that (1) the magnetic particles are maintained substantially in suspension, (2) the cells are maintained substantially in suspension, and/or (3) binding of the cells to the magnetic particles is at or near optimum (e.g., a local maximum). Agitation can be in an orbital (e.g., circular), linear, or other (e.g., irregular) motion. The specific parameters of agitation should be set to avoid spillage of the sample from the vessel and to avoid breakage of the interaction between the cells and the magnetic particles.

In some embodiments, the agitation occurs at a frequency and with an amplitude such that the magnetic particles and/or the cells are maintained substantially in suspension. For example, the sample can be shaken or vibrated such that, at steady state, a test sample removed from near the top of the liquid column in the vessel has about the same number (e.g., at least 80%, 85%, 90%, or 95% of the number) of magnetic particles or cells per unit volume as a test sample removed from near the bottom of the liquid column. Magnetic particles and/or cells can be counted by any means known in the art, e.g., using a microscope and hemocytometer or using flow cytometry.

Efficient sample mixing has been found to positively affect the yield of cells. Mixing depends on several variables such as sample volume, vessel dimensions (diameter and height), vibration frequency, and oscillation amplitude. In some embodiments, the step of agitating includes shaking or vibrating (e.g., in a circular or linear motion) the sample in a vessel at a frequency of about 200-1000 rpm (e.g., about 200-400, 300-500, 400-600, 500-700, 600-800, 700-900, 800-1000, 200-500, 300-600, 400-700, 500-800, 600-900, or 700-1000 rpm) and with an amplitude (in distance) of about 2-8% (e.g., about 2-5%, 5-8%, 2-4%, 3-5%, 4-6%, 5-7%, or 6-8%) of the height of the liquid column in the vessel or about 10-40% (e.g., about 10-20%, 15-30%, 20-35%, 30-40%, or 15-25%) of a dimension of the width of the liquid column in the vessel (e.g., a maximum diameter of the liquid column). Better results may be obtained with agitation of at least about 500 or 700 rpm.

In some embodiments, the step of agitating includes agitating, shaking, or vibrating (e.g., in a circular, or linear motion) at a frequency of about 400-1000 rpm (e.g., about 400-600, 500-700, 600-800, 700-900, 800-1000, 400-700, 500-800, 600-900, or 700-1000 rpm) and with an amplitude of about 1-20 mm (e.g., about 1-2, 1-5, 1-10, 2-5, 2-10, 2-20, 5-10, 1-3, 2-4, or 5-20 mm).

Typically, the phase relation between the mixing and liquid motion establishes a turbulent or more gentle operating condition, such that the surface of the liquid forms a smooth traveling surface wave versus a peaking of out-of-phase liquid that results in spillover and splashes. Smoother surface conditions may help to minimize breakage of cell-magnetic particle complexes.

High-Throughput Methods

The new methods described herein can be used in high-throughput methods of WBC separations. For example, the procedures can be carried out in multi-well (e.g., 4, 6, 8, 12, 24, 96, or more-well) format for simultaneous processing of multiple samples. Furthermore, all of the steps (e.g., sample and reagent additions, washing, mixing, and reagent removal) can be adapted to be performed by a standard liquid-handling robot.

Exemplary liquid handling robots include the Biomek™ FX liquid handling system (Beckman-Coulter, Fullerton, Calif.), TekBench™ automated liquid handling platform (TekCel, Hopkinton, Mass.), and Freedom EVO® automation platform (Tecan Trading AG, Switzerland).

Open top tubes and/or plates are preferred for automated protocols, because of the difficulty of opening or closing vessels by automated systems. Mixing by agitation (e.g., agitation, shaking, or vibration) is advantageous for automated systems because the parameters can be set such that closing of tubes is not required, as it is for rocking or inversion mixing. Agitation/shaking modules are available for integration in automated systems and can be adapted for use in the protocols described herein.

By use of plates or racks adapted for larger volumes (e.g., with 4, 6, 8, 12, or 24 positions), the milliliter volumes typically used in blood cell preparations can be processed by automated platforms, either in one well of the plate or rack or in parallel in more than one. If the sample is split into more than one position, the final product can be pooled to one sample. Use of a 24-position rack with 2-ml cryogenic vials has been found to be suitable for blood cell purifications.

Figure 2:
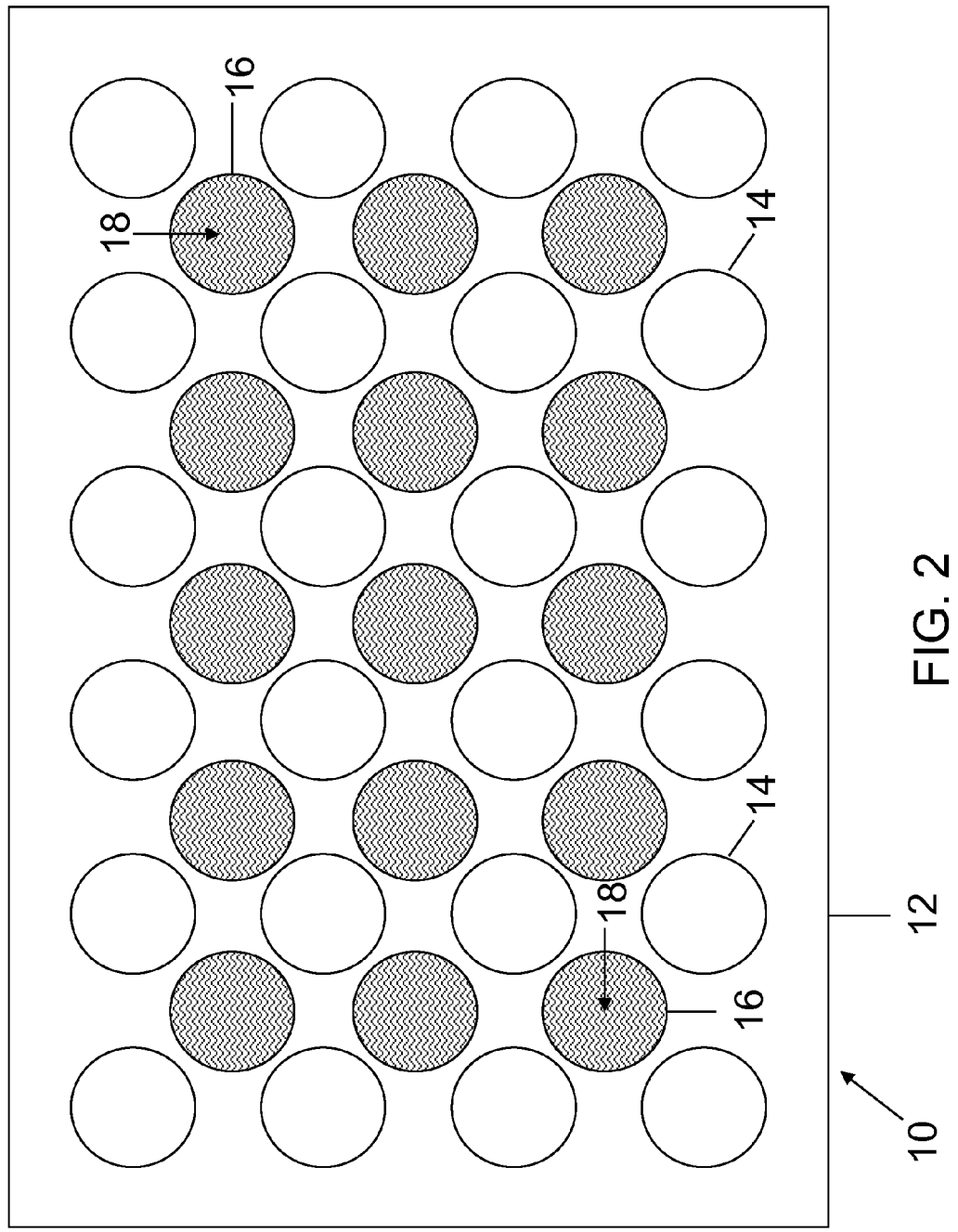
FIG. 2 is a schematic diagram of an exemplary magnet arrangement for use with a multi-well plate. The open circles represent sample positions and the shaded circles represent cylindrical magnets.

Specialized magnetic devices can be prepared for use with automated platforms. As shown in FIG. 2, an exemplary device 10 has two separate parts: a twenty-four-well adapter plate 12 with twenty-four sample positions 14 (e.g., twenty-four wells adapted to accommodate twenty-four two ml sample vessels (e.g., cryogenic vials)), and an undersurface that contains fifteen magnet positions 16 to accommodate fifteen cylindrical magnets 18. In FIG. 2, the open circles represent sample positions 14 and the shaded circles represent cylindrical magnets 18 in positions 16.

The undersurface positions are logistically placed between and in magnetic contact with the top twenty-four-well cryovial well positions such that each magnet position 16 contacts four sample positions 14. These "bottom" wells allow for the insertion/placement of cylindrical magnet(s) 18, whose field strength is used to pull the magnet beads and/or magnet-bead cell complexes to the cryovial well sides. Each cylindrical magnet fits neatly into its "home" well in the bottom the cryovial adapter plate 12. The fifteen separate (cylindrical) magnets 18 are mounted in a standing position to a metal base (to facilitate cooling). This magnet base plate footprint is the same as the twenty-four-well cryovial adapter plate 12. The fifteen separate cylindrical magnets mounted and attached in a fixed 3×5 matrix geometry allows the 24-well cryovial adapter plate to be robotically placed directly on-top-of the magnets with each magnet fitting snugly into its appropriate home well position.

This type of magnet plate system can be adapted to any commonly used microplate geometry, with the magnets placed at the intersection points between sample positions. For example, the plate can use 4 sample positions (2×2) and 1 magnet, 6 sample positions (2×3) and 2 magnets (1×2), 8 sample positions (2×4) and 3 magnets (1×3), 12 sample positions (3×4) and 6 magnets (2×3), 24 sample positions (6×4) and 15 magnets (5×3), 96 sample positions (12×8) and 77 magnets (11×7), or 384 sample positions (24×16) and 345 magnets (23×15).

Implementation

The new methods can be implemented in laboratory automation hardware controlled by a compatible software package (e.g., Biomek™ FX software) programmed according to the new methods described herein or a new software package designed and implemented to carry out the specific method steps described herein. The methods can be implemented by computer programs using standard programming techniques following the method steps described herein.

The programs should be designed to execute on a programmable computer including at least one processor, at least one data storage system (including volatile and non-volatile memory and/or storage elements, e.g., RAM and ROM), at least one communications port that provides access for devices such as a computer keyboard, telephone, or a wireless, hand-held device, such as a PDA, and optionally at least one output device, such as a monitor, printer, or website. The central computer also includes a clock and a communications port that provides control of the lab automation hardware. These are all implemented using known techniques, software, and devices. The system also includes a database that includes data, e.g., data describing the procedure of one or more method steps described herein.

Program code is applied to data input by a user (e.g., location of samples to be processed, amounts of liquid dispensed or aspirated, transfer of samples from one location in the system to another) and data in the database, to perform the functions described herein. The system can also generate inquiries and provide messages to the user. The output information is applied to instruments, e.g., robots that manipulate, heat, agitate, etc. the vessels that contain the blood samples as described herein. In addition, the system can include one or more output devices such as a telephone, printer, or a monitor, or a web page on a computer monitor with access to a website to provide to the user the results of testing (e.g., for purity, viability, and yield) of the blood samples.

Each program embodying the new methods is preferably implemented in a high level procedural or object-oriented programming language to communicate with a computer system. However, the programs can also be implemented in assembly or machine language if desired. In any case, the language can be a compiled or interpreted language.

Each such computer program is preferably stored on a storage medium or device (e.g., RAM, ROM, optical, magnetic) readable by a general or special purpose programmable computer, for configuring and operating the computer when the storage media or device is read by the computer to perform the procedures described herein. The system can also be considered to be implemented as a computer- or machine-readable storage medium (electronic apparatus readable medium), configured with a program, whereby the storage medium so configured causes a computer or machine to operate in a specific and predefined manner to perform the functions described herein.

The new methods can be implemented using various means of data storage. The files can be transferred physically on recordable media or electronically, e.g., by email on a dedicated intranet, or on the Internet. The files can be encrypted using standard encryption software from such companies as RSA Security (Bedford, Mass.) and Baltimore®. The files can be stored in various formats, e.g., spreadsheets or databases.

As used herein, the term "electronic apparatus" is intended to include any suitable computing or processing apparatus or other device configured or adapted for storing data or information. Examples of electronic apparatus suitable for use with the present invention include stand-alone computing apparatus; communications networks, including local area networks (LAN), wide area networks (WAN), Internet, Intranet, and Extranet; electronic appliances such as personal digital assistants (PDAs), cellular telephones, pagers and the like; and local and distributed processing systems.

As used herein, "stored" refers to a process for encoding information on an electronic apparatus readable medium. Those skilled in the art can readily adopt any of the presently known methods for recording information on known media to generate manufactures comprising the sequence information.

A variety of software programs and formats can be used to store method data on an electronic apparatus readable medium. For example, the data and machine instructions can be incorporated in the system of the software provided with the automated system (e.g., the Biomek™ FX software), represented in a word processing text file, formatted in commercially-available software such as WordPerfect® and MicroSoft® Word®, or represented in the form of an ASCII file, stored in a database application, such as Microsoft Access®, Microsoft SQL Server®, Sybase®, Oracle®, or the like, as well as in other forms. Any number of data processor structuring formats (e.g., text file or database) can be employed to obtain or create a medium having recorded thereon the relevant data and machine instructions to implement the methods described herein.

By providing information in electronic apparatus readable form, the programmable computer can communicate with and control the lab automation hardware to perform the methods described herein. One skilled in the art can input data in electronic apparatus readable form (or a form that is converted to electronic apparatus readable form) to describe the completion of various method steps by the lab automation hardware.

EXAMPLES

The following examples are meant to illustrate, but in no way to limit, the claimed invention.

Example 1

Gradient and Magnetic Separations

The final white blood cell (WBC) products obtained by standard gradient methods and the new magnetic separation methods described herein were compared.

WBCs were separated from whole blood using a Ficoll gradient method followed by RBC lysis. The Ficoll®

Hypaque® (Amersham Biotech) reagent was warmed to room temperature, and 15 ml of the undiluted solution was placed in the bottom of 50 ml plastic centrifuge tubes. The blood was diluted 1:3 in Hank's balanced salt solution (HBSS) without serum and carefully layered on top of the Ficoll® gradient with meticulous attention that the dispersion of fluid did not disturb the layer and cause non-specific cell loss to the pellet. These centrifuge tubes were then spun at 3000 rpm for 20 minutes in a centrifuge at room temperature. Next, a 10 ml pipette was carefully inserted into the gradient to the layers with white blood cells. About 2-3 ml of enriched white blood cells were aspirated, taking care to leave the adjacent Ficoll® substance.

Figure 3:
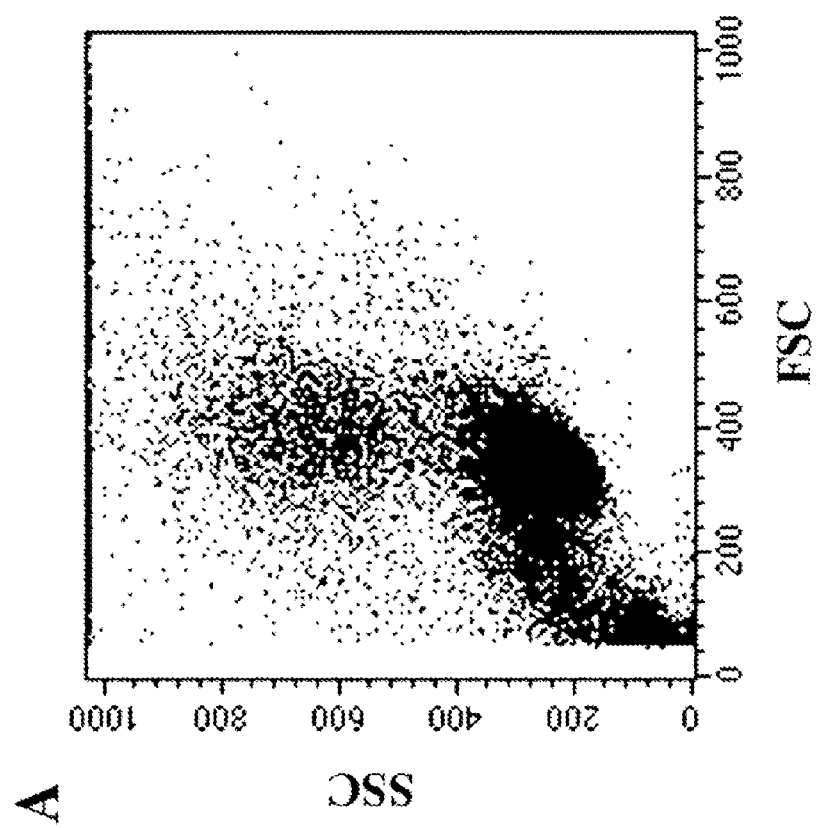
FIG. 3 is a scatter plot showing forward and side scatter for fresh blood separated by a Ficoll gradient followed by RBC lysis.

The enriched layer was then placed into another 50 ml tube and washed three more times with HBSS containing 2% serum. After the third wash, the cells were pelleted by centrifugation. To eliminate contaminating RBCs, the mostly dry pellet was treated with $NH_4Cl$ (PharM Lyse™, Becton Dickinson) to lyse the RBCs. After a 3-4 minute incubation, the cells were washed three more times to eliminate the $NH_4Cl$ and to add fresh media to the sample. The final cell product was analyzed by flow cytometry (FIG. 3). FIG. 3 shows a large number of dead cells in the lower left corner of the plot. Additionally, the sample shows a large amount of variability of light scattering properties, indicating low cell purity.

Figure 4:
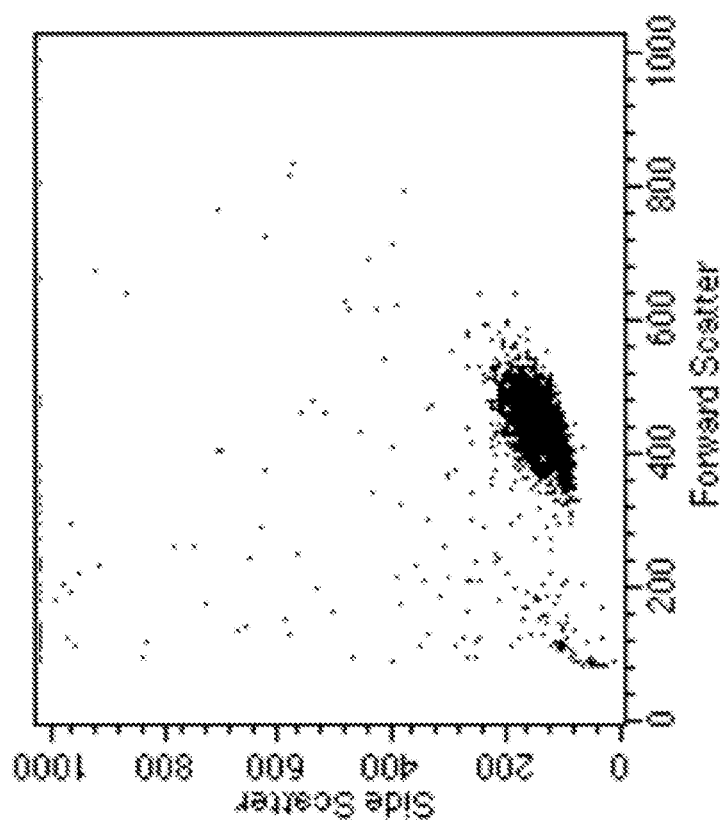
FIG. 4 is a scatter plot showing forward and side scatter for fresh blood separated by the new methods to prepare a population of $CD8^+$ cells.

$CD8^+$ WBCs were also separated magnetically using the new methods described herein. Briefly, 5-7 ml of whole blood were diluted with 10-20 ml of Hank's balanced salt solution (HBSS; 0.4 mM $KH_2PO_4$, 0.6 mM $MgSO_4$, 5.4 mM KCl, 1.3 mM $CaCl_2$, 0.5 mM $MgCl_2$, 5.6 mM D-Glucose, 0.3 mM $Na_2HPO_4$, pH 7.4) with 2% fetal bovine serum (FBS). Pre-washed DYNABEADS® CD8 (Dynal Biotech, Oslo, Norway) magnetic beads were added to the diluted whole blood. The mixture was incubated for 45 minutes at 4° C. with gentle shaking, and the $CD8^+$ cells were separated by placing the thin-walled sample tube in a magnetic device for 2-10 minutes. The supernatant was removed by pipette, and the bound cells were washed four times with HBSS/2.5% FBS. After the second wash, the cells were allowed to rebind for 10 minutes before removal of supernatant. Following the four washes, $CD8^+$ cells were removed from the DYNABEADS® CD8 by incubation with DETACHABEADS® (Dynal Biotech) beads. The supernatant, which contained the $CD8^+$ cells, was transferred to a fresh tube. The cell product was analyzed by flow cytometry (FIG. 4). As shown in FIG. 4, the cells were highly homogeneous, with few obvious dead cells.

This example demonstrates that the new methods yield high-quality preparations of white blood cells compared to a known Ficoll® gradient method.

Example 2

Comparison of Magnetic Separation Methods

Six fresh blood samples were divided and each was simultaneously processed to isolate white blood cells by three methods. Cells were separated using Whole Blood CD8 Microbeads system from Miltenyi Biotec (Bergisch Gladbach, Germany) according to the manufacturer's instructions, CD8 Positive Isolation kit from Dynal Biotech according to the manufacturer's instructions, or the magnetic separation method described in Example 1. The final cell preparations obtained by using the three methods were analyzed for cell yield, viability, and purity (Table 1).

Cell yield was estimated by comparing the number of cells obtained, as measured by flow cytometry, to an estimate of the average number of $CD8^+$ cells in human blood ($0.388 \times 10^6$ cells/ml). The average observed cell yield using the new method (87%) was approximately twice the average yield obtained using the Dynal method (44%), and more than four times the average yield obtained using the Miltenyi method (18.3%). The new methods gave a superior $CD8^+$ cell yield.

Viability and purity of the isolated $CD8^+$ cells were measured using flow cytometry. 50 µl of cell preparation were mixed with 200 µl of 5 µg/ml propidium iodide (PI) and 3 µl of FITC-conjugated anti-CD8 antibody. Dead cells were identified by PI fluorescence, whereas $CD8^+$ cells had fluorescence from FITC. The highest viability was observed using the new methods (97%), whereas the Dynal and Miltenyi methods gave lower viability (90% and 86%, respectively). $CD8^+$ cell purity was nearly equivalent among the three methods, all of which gave approximately 90% CD8+ cells (91% for Miltenyi, 89% for Dynal and new methods).

This example demonstrates that the new methods produce white blood cell preparations with higher yield, viability, and purity than known magnetic separation methods.

TABLE 1

Comparison of whole blood separation methods for individual blood samples simultaneously processed by three methods

| Sample | Miltenyi | Dynal | New Methods |
|---|---|---|---|
| Cell yield (%) | | | |
| 1 | 25 | 55 | 86 |
| 2 | 15 | 35 | 82 |
| 3 | 11 | 40 | 90 |
| 4 | 21 | 45 | 92 |
| 5 | 20 | 41 | 88 |
| 6 | 18 | 48 | 85 |
| Average | 18.3 | 44 | 87 |
| Viability (% $PI^-$ cells) | | | |
| 1 | 85 | 92 | 98 |
| 2 | 80 | 92 | 99 |
| 3 | 86 | 94 | 92 |
| 4 | 88 | 88 | 98 |
| 5 | 90 | 88 | 98 |
| 6 | 87 | 89 | 97 |
| Average | 86 | 90 | 97 |
| Purity (% $CD8^+$ T cells) | | | |
| 1 | 95 | 90 | 85 |
| 2 | 90 | 85 | 98 |
| 3 | 88 | 86 | 86 |
| 4 | 88 | 86 | 86 |
| 5 | 94 | 96 | 88 |
| 6 | 90 | 92 | 90 |
| Average | 91 | 89 | 89 |

Samples represent normal blood drawn and the processed on the same, day but by 3 different methods.
Cell yield is the calculated numbers of CD8 cells retrieved from 1 cc of blood. T cells: 70-80%: CD4+ 50-70% $CD8^+$ 10-30%

Example 3

Impact of Tube Design on Yield of Cells

Cell yield can be optimized by using a sample vessel with thin walls and a vessel design that maximizes sample proximity to the magnet device, in this case, round-bottom tubes that are not tapered. In this example, a semi-cylindrical magnet was used with nearly cylindrical sample tubes. Tube A was a Becton Dickinson centrifuge tube (sterile) #352097 (wall thickness of 0.76 mm), and Tube B was a Becton Dickinson centrifuge tube (sterile) #352054 (wall thickness of 0.64 mm). Both Tube A and Tube B are routinely used for cell culture experiments and are made of plastic. These tubes vary by two major features. Tube A has thick walls and a long tapered design. Tube B has thin walls and straight sides followed by a small round bottom without a taper.

Magnetic separations were performed as described above using either Tube A or Tube B. As Table 2 shows, the increased thickness of the Tube A walls plus the tapered walls had an impact on yield of CD8$^+$ T cells from fresh human blood. Tube A had an average yield of 58%, whereas Tube B had an average yield of 88%. For the two different tube designs, there was no impact on viability or purity on the CD8 cell preparations.

TABLE 2

Effect of vessel design on yield

| Sample | Yield of CD8 Cells/ml Blood (% yield of whole blood) | |
|---|---|---|
| | Tube A | Tube B |
| #1 | 61 | 85 |
| #2 | 52 | 92 |
| #3 | 64 | 90 |
| #4 | 42 | 87 |
| #5 | 71 | 86 |
| Average | 58 | 88 |

Example 4

Impact of Time Adjacent to the Magnet on Cell Yield

Based on the principles of magnetic force, efficiency can be increased by either allowing the magnetic force an opportunity to pull longer (time) or allowing the magnetic force an opportunity to have repeat exposure to the magnet (re-circulations or re-peat separations). Magnetic separations were performed as described above using a first magnetic exposure of 30 or 60 minutes. Table 3 shows the effect of 30 minute and 60 minute magnetic exposure times on separation of samples of whole blood. Using a 60 minute first magnetic exposure during the separation protocol gave a more than two-fold better average yield than a 30 minute first magnetic exposure, 80% versus 35%. The longer exposure to the magnet did not alter viability or purity.

TABLE 3

Effect of Magnetic Exposure Time on Yield

| Sample | Yield of CD8 Cells/ml Blood (% yield of whole blood) | |
|---|---|---|
| | 30 minutes | 60 minutes |
| #1 | 23 | 85 |
| #2 | 43 | 82 |
| #3 | 49 | 81 |
| #4 | 26 | 72 |
| Average | 35 | 80 |

Example 5

Impact of Sample Viscosity on Cell Yield

Magnetic separations were performed as described above using either whole blood or whole blood that was washed times with HBSS (Hanks Balanced Salt solution) with 5% FBS (fetal bovine serum) and an anti-coagulant (ACD) to reduce the viscosity. As shown in Table 4, the washed blood gave a nearly three-fold better average yield than the whole blood without washing, 87% versus 30%. This indicates that a decrease in viscosity of the whole blood sample can increase cell yield.

TABLE 4

Effect of Washing on Yield

| Sample | Yield of CD8 Cells/ml Blood (% yield of whole blood) | |
|---|---|---|
| | Washed Blood | Whole Blood |
| #1 | 82 | 10 |
| #2 | 85 | 22 |
| #3 | 90 | 35 |
| #4 | 92 | 55 |
| Average | 87 | 30 |

Example 6

Impact of the New Methods in a Viability Assay

Magnetic separations were performed by the three methods described in Example 2 using whole blood as the starting material. As demonstrated above, these methods vary in cell yield, cell viability, and cell purity. We used these three different cell preparations in a functional assay. In this assay, isolated CD8 cells from a type 1 diabetic and a control individual are exposed to TNF. In a trait specific to type 1 diabetes, a minor subpopulation of CD8 cells of type 1 diabetics die upon TNF exposure. This assay requires CD8 cells that are representative of the entire blood population and are of high purity so specific killing can be detected. Cell death was measured using the LDH ELISA assay. A high LDH OD indicates cell death, whereas a low LDH OD means sustained viability or proliferation.

The killing effect of TNF on the subpopulation of sensitive cells in the diabetic samples as compared to the non-diabetic samples was observed only with cells prepared using the new methods, and not with cells prepared by the Dynal or Miltenyi methods.

TABLE 5

Functional data of TNF killing of type 1 diabetic cells purified by three different methods in a LDH ELISA assay (LDH OD %)

| Sample TNF dose (ng/ml) | Miltenyi (Control/Diabetic) | Dynal (Control/Diabetic) | New Methods (Control/Diabetic) |
|---|---|---|---|
| 0 | 0/0 | 0/0 | 0/0 |
| 0.1 | −9/−3 | +5/+5 | −5/+5 |
| 2.5 | +1/+5 | +8/+9 | −12/+15 |
| 5 | +8/+8 | +9/+24 | −12/+12 |
| 10 | +22/+24 | +28/+26 | −16/+10 |
| 20 | +24/+26 | +22/+27 | −12/+5 |

Table 5 shows the results of killing of type I diabetic cells obtained by the three methods shown at the listed concentrations of TNF. The numbers given are percent change in ELISA OD (optical density) compared to the same sample without TNF addition. These results indicate that the cell preparations made according to the new methods contain CD8 cells that are representative of the entire blood population and are of high purity. The same was not true for the cell preparations made by the Dynal or Miltenyi methods.

Example 7

Influence of Agitation on Mixing and Cell Yield

Magnetic beads and cells settle in the tubes with the passage of time based on the viscosity of the medium and particle density. The rate of settling of beads and cells were determined to be 0.4 mm/minute and 0.12 mm/minute, respectively for beads and cells.

To demonstrate efficiency of mixing, a small number of magnetic beads was added to water and added in 1 ml or 2 ml aliquots to 2 ml cryogenic vials (Prod. No. 430661, Corning Life Sciences, Acton, Mass.). The vials were placed in a 24-Place Rack (Part No. 373661, Beckman Coulter, Fullerton, Calif.), which is useful for adapting procedures to automated platforms such as the Biomek® Automated Workstations (Beckman Coulter). The samples were shaken on a Variomag Thermoshake™ (Inheco, Munich, Germany) agitator at the indicated frequencies (Table 6). Samples were taken from near the top and bottom of the liquid sample at the times indicated and the number of particles was counted using a hemocytometer. The results, shown in Table 6, show efficient mixing (less than 10% difference between the number of particles at the top and bottom of the tube) under most of the conditions tested.

TABLE 6

Mixing of Magnetic Particle Samples

| Mixing Conditions | Sample Location | 1 ml in 2 ml vial | 2 ml in 2 ml vial |
| --- | --- | --- | --- |
| 825 rpm, 30 min. | top: | 94 | 128 |
| | bottom: | 69 | 122 |
| 825 rpm, 60 min. | top: | 130 | 123 |
| | bottom: | 119 | 129 |
| 750 rpm, 15 min. | top: | 108 | 105 |
| | bottom | 119 | 113 |

Some lower frequencies than indicated above, yielded a larger number of particles at the bottom than at the top, suggesting that settling was taking place. Also, at higher frequencies (e.g., above 900 rpm), greater spillage occurred unless the sample volume was less than 2 ml. Also, we often saw a greater number of beads at the top than at the bottom, indicating that the mixing is driving more beads to the top.

CD8+ cells were prepared by magnetic separation as described in Example 1, but with the gentle shaking step as follows. The 2 ml sample was shaken at 800 rpm on a Variomag Thermoshake™ Mixer (Inheco) at 4° C. for 10 minutes, followed by an aspirate dispense step. This agitation/aspiration process was then repeated three times. The repeated agitation/aspiration step was performed during both the bead attachment and detachment steps. This protocol yielded a WBC preparation of higher yield compared to the same method with a rotary mixer (Table 7). This example indicates that agitation can improve mixing and cell yield in methods of magnetic separation of WBCs compared to the use of rotation.

TABLE 7

Impact of Vibration vs. Rotation on Increasing Sample Yield

| | Sample trait |
| --- | --- |
| Blood separation with vibration | |
| Yield ($\times 10^6$/ml) | 0.51 |
| Viability (%) | 98.8 |
| Purity (%) | 99.5 |
| Blood separation with rotation | |
| Yield ($\times 10^6$/ml) | 0.22 |
| Viability (%) | 97 |
| Purity (%) | 99.2 |

Example 8

Manual Separation Protocol

This example outlines an exemplary procedure for producing a CD8+ WBC preparation by the improved methods using manual steps.

Prior to using the DynaBeads® CD8 (Dynal Biotech, Oslo, Norway), the beads were washed to remove azide and/or other preservatives. The CD8 magnetic beads were mixed thoroughly in the vial by shaking on a rocker in a cold room at 4 C for 15 minutes. Twenty μl of the bead suspension per ml of blood to be processed (400 μl total) was transferred to a 15 ml conical tube. 12 ml of wash buffer (HBSS+2% FBS, with or without phenol, no antibiotics) was added to the CD8 beads, and the beads were mixed up and down by shaking. The lid of the tube was opened and the tube was placed in a magnetic device for 5 minutes until the sample cleared. The supernatant was removed using a pipette and the wash step was repeated with 12 ml of wash buffer. The washed magnetic beads were resuspended with 1200 μl wash buffer and kept at 4° C. until use.

Approximately 20 ml of blood sample from one person was processed using these methods. A complete blood count (CBC) of the sample was performed prior to processing for later calculation of the final yield. The 20 ml blood sample was transferred to a 50 ml conical tube using a pipette. The original tubes were washed with 10 ml of wash buffer and the wash was also add to the 50 ml conical tube with the blood sample. 7 ml of the anticoagulant ACD (citrate-dextrose solution) were added to the blood with additional wash buffer to a total volume of 45 ml. The sample was mixed by shaking up and down and centrifuged at ~1450 rpm (~300-400 g) for 8 minutes at 4° C.

Following the spin, the sample was allowed to sit for two more minutes to make sure that all of the cells settled at the interface. The supernatant was removed carefully with a 10 ml pipette, taking care not to pipette any cells and leaving 2-3 ml of liquid above the interface. The cells were washed twice more by adding 7 ml ACD, bringing the volume to 45 ml with wash solution and centrifuging as above. After the third wash, the supernatant was light yellow and separated well from the blood cells.

After the last centrifuge, the supernatant was again removed very carefully using a pipette, such that as much of the supernatant was removed as possible, but leaving some so as not ensure cells were not pipetted. The sample was mixed using a 5 ml pipette and dispensed equally into three new 15 ml tubes. The original 50 ml tube was washed with about 3 ml wash solution and likewise transferred equally to the new tubes.

400 µl of the washed CD8 beads were added to each of the 15 ml tubes containing the blood cells. The tubes were caped and the sample mixed by shaking up and down several times. The tubes were then transferred to a rocker in the cold room (4° C.) for 40 minutes to allow binding of the beads to the cells.

After 40 minutes, the tubes were removed from the cold room, and 800 µl of buffer was used to wash the lid and walls of each tube and added to the main sample for a final volume of about 8 ml. The tubes were incubated on ice for 4 minutes and then placed on the magnet for 10 minutes. The supernatant was removed from each of the three tubes with a 10 ml pipette, and 2 ml wash buffer was immediately added to wash the cells from the tube wall. The cells from all three tubes were transferred to a new 15 ml tube, and the three original tubes were washed consecutively with 2 ml wash buffer, with the volume transferred to the new tube for a final volume of ~8 ml. The cells were mixed up and down 30 times with a 10 ml pipette and left on ice for 10 minutes.

The cells were placed in the magnetic field for 10 minutes, and the supernatant removed using a 10 ml pipette. 2 ml wash buffer was added to the cells and mixed, and the cells were transferred to a 12×75 mm FACS tube. The original tube was washed once with 2 ml wash buffer, and the liquid was also added to the FACS tube for a final volume of ~4 ml. The cells were mixed by pipetting up and down vigorously ~30 times, incubated on ice for 10 minutes, and then placed in the magnetic field for 6 minutes.

The cells were resuspended in 2 ml wash buffer and transferred to a new FACS tube, with the tube washed with 2 ml buffer which is also transferred as before. The cells were mixed, incubated on ice for 10 minutes, and placed in the magnetic field for 6 minutes. The steps of this paragraph were repeated, and the final pelleted cells were resuspended using 1200 µl 10% FBS buffer (RPMI+10% FBS+1% penicillin/streptomycin and kanamycin). At this step, the sample contains purified cell bead complexes.

The sample was dispensed in 400 µl aliquots to each of three micro-centrifuge tubes, each containing 80 µl of Dynal DETACHABEAD® solution. The samples were mixed and incubated at room temperature for 1 hour. The contents of the three tubes were then transferred into a 15 ml tube. The micro-centrifuge tubes were each washed 2-3 times with 10% FBS buffer and the wash also added to the 15 ml tube for a final volume of about 4 ml. The sample was mixed by pipetting up and down 30 times.

The tube was placed in the magnetic field for, and the supernatant was immediately transferred into a new 15 ml tube (on ice) using a 1 ml pipette.

The pelleted beads were then washed with 2 ml buffer, pipetted up and down 30 times, and placed on the magnetic field. Again, the supernatant was immediately transferred to the 15 ml tube containing the previous supernatant. The beads were washed and placed in the magnetic field 4 more times. Each time the supernatant was added to the 15 ml tube. The last two times, only 1 ml buffer was used instead of 2 ml. The final volume of supernatant was ~12 ml.

The supernatant containing the cells was placed on the magnetic field for 6 minutes. The supernatant was removed to a new 15 ml tube. The pipette was left in the tube for 5-10 min to let all the cells flow down before transfer.

The cells were mixed well using a 10 ml pipette. 15 µl were added to 15 µl trypan blue for counting. The remainder of the sample was spun down at 4200 rpm and resuspended at $1\times10^6$ cells/ml with 10% FBS.

To count the cells for viability, purity, and yield, 50 µl of the final cell sample were added to a FACS tube containing 200 µl PI (propidium iodine) and 3 µl of anti-CD8-FITC. The sample was mixed and incubated at room temperature in the dark for 15 minutes. The sample was analyzed by FACS (Becton Dickinson, Franklin Lakes, N.J.). Yield was estimated by comparing the number of cells obtained to the numbers from the complete blood count carried out on the small sample removed initially. The small sample was counted for CBC on a Coulter Counter. On average T cells make up approximately 40% of the white blood cell CBC count, and the ratio of CD4 and CD8 cells is known to be 3:1.

Example 9

Automated Separation Protocol

This example outlines an exemplary procedure for producing a $CD8^+$ WBC preparation by the improved methods.

This protocol was performed using a Biomek® FX Laboratory Automation Workstation (Beckman Coulter, Fullerton, Calif.). The workstation was prepared according to manufacturer's instructions by starting the instrument with a Thermoshake™ module and Peltier cooling modules. A 24-space plate adapted for use with a specially designed magnetic plate and the automation system (as shown in FIG. 2) was placed in the cold room with a 2 ml cryogenic vial in each space. A pack of 1 ml disposable pipetting heads was also placed in the cold room. Buffer reservoirs were prepared with HBSS wash solution and RPMI medium and kept at 4° C. until use.

Dynal DYNABEADS® CD8 were washed prior to use as described in above Examples, resuspended with 1200 µl wash buffer, and kept at 4° C. until use.

Approximately 20 ml of fresh blood was prepared by washing as described in Example 8 three times until the supernatant was light yellow and well separated from the blood cells. Prior to the wash, a small sample was taken for complete blood count (CBC). After carefully removing the supernatant, the blood cells were mixed by pipetting up and down.

The washed beads were added to the 50 ml tube containing the washed blood cells and the sample was shaken by hand. The 24-well plate was retrieved from the cold room, 2 ml of the blood/bead sample was added to each of 8 cryogenic vials of the plate. If the blood/bead sample was less than 16 ml total, the 50 ml tube was rinsed with an appropriate amount of wash buffer to make 16 ml, and the wash was added to the cryogenic vials. Care was taken to keep the pipette tip from touching the vial sides. Any spillage was wiped with a sterile cotton swab. The plate with cryogenic vials containing the cell/bead sample was placed on the Thermoshake™ vibration module on the deck of the automation system.

To bind the beads to the cells, the automation system was configured to perform the following steps on the cell/bead sample in the magnetic plate. Each vial containing the sample was mixed by aspirating and dispensing 900 µl of the sample in each vial using the cold pipetting heads. The vibration module then agitated the sample for 10 minutes at 800 rpm and 10° C. The system then repeated the mixing and agitation steps three additional times. The samples were then mixed a final time by aspirating and dispensing 925 µl of the sample in each vial using the cold pipetting heads. The plate was moved from the agitation module to the magnet on a Peltier cooling module to a temperature range characteristic of a refrigerator range, but without freezing the cells and media at 4-8° C., by the automation system and allowed to sit for two minutes to allow the magnet to bind the bead/cell complexes.

To wash the bead/cell complexes, the automation system was configured to perform the following steps. A 925 μl aliquot of the supernatant was transferred from each cryogenic vial on the magnetic plate to waste, followed by another 925 μl aliquot and a 400 μl aliquot. The system removed the plate from the magnet and 925 μl HBSS wash buffer was added twice to each sample vial. The plate was moved from the agitation module to the magnet on a Peltier cooling module by the automation system and allowed to sit for two minutes to allow the magnet to bind the bead/cell complexes. Two 925 μl aliquots of the supernatant were transferred from each cryogenic vial on the magnetic plate to waste, followed by a 200 μl aliquot.

The plate was again removed from the magnet by the automation system and 2×925 μl HBSS wash buffer was added to each sample vial. The plate was moved onto the magnet allowed to sit for 2 minutes. 2×925 μl was transferred from each vial to waste. The sample was removed from the magnet and 100 μl RPMI was transferred to each vial.

The samples were pooled and the sample was processed following the steps for detachment and analysis in Example 8. Optionally, the detachment steps are adapted for use in the Biomek™ FX system.

In such an automated detachment step, the DETACHA-BEAD® solution is added to the samples, they are mixed up and down by aspiration/dispensing, and the sample is mixed by six repetitions of aspiration/dispensing followed by 10 minutes agitation on the Thermoshake™ at 800 rpm. The plate is then moved to the magnet for two minutes to allow binding of the detached beads. The supernatant containing the cells is transferred to one or more new vials. The beads are washed 2-4 times by adding RPMI, moving to the magnet to allow binding, and transferring the supernatant containing cells to the new vials.

Example 10

The New Methods Improve Purity, Viability, and Yield

CD8+ T cell preparations were made from fresh human blood using a standard Ficoll gradient method followed by magnetic separation using DYNABEADS® CD8 (Dynal Biotech, Oslo, Norway) (n=44), DYNABEADS® CD8 according to the manufacturer's instructions (n=149), and DYNABEADS® CD8 essentially according to the protocol in either Example 1 or Example 8 (n=273). Table 8 shows the frequency of results obtained for each level of purity, viability, and yield as a percentage of the total number of samples prepared. Purity was measured as % CD8 T cells using flow cytometry analysis, and viability was measured used PI staining and flow cytometry. Yield was calculated as the percentage of CD8+ cells compared to the number obtained from a simultaneously performed complete blood cell count on a parallel sample. The new methods ("modified magnetic method") consistently produced cell preparations of higher purity, viability, and yield than the unmodified magnetic method or the gradient method.

TABLE 8

Comparison of Three Manual Methods on Fresh Blood Samples

|  | Gradient Method | Unmodified Magnetic Method | Modified Magnetic Method |
|---|---|---|---|
| Purity |  |  |  |
| >90% | 0 | 26.8 | 58.6 |
| 80-90% | 0 | 67.1 | 39.9 |
| <80% | 100 | 6.0 | 1.5 |
| Viability |  |  |  |
| >90% | 0 | 0 | 95.2 |
| 80-90% | 0 | 65.8 | 3.7 |
| <80% | 100 | 34.2 | 1.1 |
| Yield |  |  |  |
| >90% | 0 | 0 | 44.7 |
| 80-90% | 0 | 0 | 53.1 |
| 70-80% | 0 | 0 | 2.2 |
| 60-70% | 0 | 58.4 | 0 |
| <60% | 100 | 41.6 | 0 |

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A method of isolating white blood cells from a whole blood sample, the method comprising:
   (a) obtaining a sample comprising whole blood;
   (b) decreasing viscosity of the sample;
   (c) contacting the sample with a magnetic particle that binds specifically to white blood cells or a subset of white blood cells to provide a white blood cell/magnetic particle complex; and
   (d) isolating the white blood cell/magnetic particle complex from the whole blood sample by subjecting the white blood cell/magnetic particle complex to a magnetic field at a strength and for a time sufficient to achieve a final cell yield of greater than 75% and a white blood cell viability of greater than 90%.

2. The method of claim 1, wherein decreasing viscosity comprises washing cells in the sample.

3. The method of claim 2, wherein washing comprises use of an isotonic solution comprising a proteinaceous additive.

4. The method of claim 3, wherein the isotonic solution is Hank's balanced salts solution comprising 2 to 5% serum.

5. The method of claim 1, wherein the white blood cell/magnetic particle complex is subjected to a magnetic field in a vessel with walls less than about 0.65 mm thick.

6. The method of claim 1, wherein the white blood cell/magnetic particle complex is subjected to a magnetic field in a vessel such that the white blood cell/magnetic particle complex is within 4 mm of a source of the magnetic field.

7. The method of claim 1, further comprising adding an anticoagulant to the sample or the white blood cell/magnetic particle complex.

8. The method of claim 1, further comprising agitating the white blood cell/magnetic particle complex at 700-900 rpm.

9. A composition of white blood cells with a white blood cell yield of greater than 75% and a white blood cell viability of greater than 90%, compared to a blood sample comprising whole blood, prepared by the method of claim 1.

10. The composition of claim 9, wherein the white blood cell viability is greater than 95%.

11. The composition of claim 9, wherein the white blood cell purity is greater than 85%.

12. A method of isolating white blood cells from a whole blood sample, the method comprising:
   (a) obtaining a sample comprising whole blood;
   (b) contacting the sample with magnetic particles that bind specifically to white blood cells or a subset of white blood cells, while agitating the blood at 700-900 rpm at an amplitude of about 2% to 8% of a height of the sample in a vessel and for a time sufficient such that the white blood cells and magnetic particles in the whole blood sample are substantially uniformly distributed throughout the sample and form white blood cell/magnetic particle complexes; and
   (c) isolating the white blood cell/magnetic particle complexes by subjecting the white blood cell/magnetic particle complexes to a magnetic field at a strength and for a time sufficient to achieve a final cell yield of greater than 75% and a white blood cell viability of greater than 90%.

13. The method of claim 12, wherein agitating comprises oscillating vessels containing the blood samples at an amplitude of 1 to 4 mm.

14. The method of claim 12, wherein the white blood cell/magnetic particle complex is subjected to a magnetic field in a vessel with walls less than about 0.65 mm thick.

15. The method of claim 12, wherein the white blood cell/magnetic particle complex is subjected to a magnetic field in a vessel such that the white blood cell/magnetic particle complex is within 4 mm of a source of the magnetic field.

16. The method of claim 12, further comprising decreasing viscosity of the sample prior to contacting the sample with the magnetic particle.

17. The method of claim 12, further comprising adding an anticoagulant to the sample or the white blood cell/magnetic particle complex.

18. A composition of white blood cells with a white blood cell yield of greater than 75% and a white blood cell viability of greater than 90%, compared to a blood sample comprising whole blood, prepared by the method of claim 12.

19. The composition of claim 18, wherein the white blood cell viability is greater than 95%.

20. A method of isolating white blood cells from a whole blood sample, the method comprising:
   (a) obtaining a sample comprising whole blood;
   (b) decreasing viscosity of the sample by washing the sample with an isotonic solution comprising a proteinaceous additive;
   (c) contacting the sample with a magnetic particle that binds specifically to white blood cells or a subset of white blood cells, while agitating the sample at 700-900 rpm to provide a white blood cell/magnetic particle complex; and
   (d) isolating the white blood cell/magnetic particle complex by subjecting the white blood cell/magnetic particle complex to a magnetic field at a strength and for a time sufficient to achieve a final cell yield of greater than 75% and a white blood cell viability of greater than 90%.

* * * * *